US010131586B2

(12) United States Patent
Chelle et al.

(10) Patent No.: US 10,131,586 B2
(45) Date of Patent: Nov. 20, 2018

(54) SOLID INOCULUM CARRIED IN A SUPERABSORBENT AGRO-PELLET WITH A VARIABLE VOLUME, OPERATING IN A NATURAL MINIFERMENTER, AND PRODUCTION METHOD

(71) Applicant: AB7 INNOVATION S.A.S.U., Deyme (FR)

(72) Inventors: Rene Chelle, Grepiac (FR); Urbain Makoumbou, Frouzins (FR)

(73) Assignee: AB7 Innovations S.A.S.U., Deyme (FR)

( * ) Notice: Subject to any disclaimer, the term of this patent is extended or adjusted under 35 U.S.C. 154(b) by 254 days.

(21) Appl. No.: 14/906,024

(22) PCT Filed: Jul. 22, 2014

(86) PCT No.: PCT/FR2014/000173
§ 371 (c)(1),
(2) Date: Jan. 19, 2016

(87) PCT Pub. No.: WO2015/007964
PCT Pub. Date: Jan. 22, 2015

(65) Prior Publication Data
US 2016/0152525 A1    Jun. 2, 2016

(30) Foreign Application Priority Data
Jul. 19, 2013 (FR) ..................................... 13 01727

(51) Int. Cl.
*C05F 11/08* (2006.01)
*C05G 3/00* (2006.01)
(Continued)

(52) U.S. Cl.
CPC ............ *C05G 3/0047* (2013.01); *C05F 11/08* (2013.01); *C12N 1/04* (2013.01); *C12N 1/14* (2013.01);
(Continued)

(58) Field of Classification Search
None
See application file for complete search history.

(56) References Cited

U.S. PATENT DOCUMENTS 3,589,364 A * 6/1971 Dean ........................ A61L 15/28
  162/146
3,661,815 A * 5/1972 Smith ........................ A23L 3/40
  525/54.32
(Continued)

FOREIGN PATENT DOCUMENTS

FR   2780725   * 1/2000
FR   2990943   * 11/2013

*Primary Examiner* — Wayne A Langel
(74) *Attorney, Agent, or Firm* — Klauber & Jackson LLC

(57) ABSTRACT

The invention relates to a solid inoculum carried in a superabsorbent agro-pellet with a variable volume, operating in a natural mini fermenter preloaded with an anhydrous nutritive medium, encouraging rapid regrowth of the viable micro-organisms and the continuous multiplication thereof. The liquid inoculum incorporated into the carrier at a low density of microbial cells is preferably comprised between $\frac{1}{500}$e and $\frac{1}{10}$e of the density recommended by the norm for a liquid inoculum of the same strain. The bioaugmentation of the microbial population is between 104 and 106 additional microbial cells. The solid inoculum according to the invention allows the preservation of the microorganisms and the handling thereof in advantageous conditions. It is not exposed to soil leaching caused by water. Said inoculum is used for the biological treatment of crops for the development and/or the preservation thereof from parasite attacks.

16 Claims, 1 Drawing Sheet

(51) Int. Cl.
  *C12N 1/04*    (2006.01)
  *C12N 1/14*    (2006.01)
  *C12N 1/20*    (2006.01)
  *C12N 1/22*    (2006.01)
  *C12N 11/02*   (2006.01)
  *C12N 11/10*   (2006.01)
  *C12N 11/12*   (2006.01)

(52) U.S. Cl.
  CPC ............... *C12N 1/20* (2013.01); *C12N 1/22* (2013.01); *C12N 11/02* (2013.01); *C12N 11/10* (2013.01); *C12N 11/12* (2013.01)

(56) References Cited

U.S. PATENT DOCUMENTS

| | | | | |
|---|---|---|---|---|
| 3,935,099 A | * | 1/1976 | Weaver | A23C 1/16 |
| | | | | 210/689 |
| 4,975,105 A | * | 12/1990 | Kremer | A01G 1/048 |
| | | | | 424/93.3 |
| 2015/0101373 A1 | * | 4/2015 | Munusamy | A01N 63/00 |
| | | | | 71/7 |

* cited by examiner

SOLID INOCULUM CARRIED IN A SUPERABSORBENT AGRO-PELLET WITH A VARIABLE VOLUME, OPERATING IN A NATURAL MINIFERMENTER, AND PRODUCTION METHOD

This application is a U.S. National Phase under 35 USC § 371 of PCT/FR2014/000173, filed Jul. 22, 2014, which claims the benefit of French Patent Application No. FR 1 301 727, filed Jul. 19, 2013. Applicants claim the benefits of 35 U.S.C. § 120 as to the PCT application and priority under 35 U.S.C. § 119 as to the French patent application, and the disclosures of both applications are incorporated herein by reference in their entireties.

The present invention relates to the field of biotic stimulator auxiliary technologies, useable in agriculture and agronomy as a partial or total substitution for fertilizer and/or phytosanitary treatment.

It is known that inocula are bacteria or microscopic fungi which are introduced into soil in order to improve plant development by:
 releasing nutrients into the soil, which are used by the plant,
 establishing symbiotic relationships with the root system of the plant to enable the plant to accomplish vital functions, such as atmospheric nitrogen fixation and use,
 acting to protect the plant from pathogens.

To this effect, rhizobacteria, which create nodules on the roots of leguminous plants, are the most commonly used, as are mycorrhizal fungi which colonize roots, enabling most types of plant to retain water and improve their nutrient absorption. Non-pathogenic microorganisms can be used in inoculation, including (using genus appellations and not limited to) for example: *Azotobacter* spp., *Acidovorax facilis*, *Bacillus subtilis*, *Flavobacterium* spp., *Pseudomonas* spp., *Rhodococcus rhodochrous*, *Bacilluschitinoporus*, *Bacilluslaterosporus*, and other genuses. For plant protection, there are also microorganisms which offer preventive benefits. These include, but are not limited to: *Bacillus thuringiensis*, *Saccharopolyspora spinosa*, *Meterhizium anisopliae* and *Beauvaria bassiana*.

Commercial inocula are available in powder, granulate and liquid form. As a general rule, powdered peat is the preferred support; mineral supports as kaolinite and vermiculite, are also used, but to a lesser degree. Inocula are sometimes applied directly to the seeds.

The international application patent WO 2004/112462 (Dec. 29, 2004) describes a support created from animal bone carbon black in the form of a granulate ranging from 0.001 mm to 10 mm, which can be used to provide natural phosphorous, biological soil pathogen control, soil decontamination and fertilisation. However, this document refers the patent WO 96/37433, which targets a disadvantage in this type of support due to a production process which requires acid and alkaline solution treatment which are undesirable for the immobilisation and conservation of microbial inocula, from a physicochemical and biological point of view. Another disadvantage of this type of material is its high water-solubility, which significantly decreases the biological benefits of the culture. This type of support will permit the acceleration of microbial growth without necessarily extending the reproduction time available for the microbial strain. This is also the same result obtained and described in U.S. Pat. No. 5,173,424, which uses the addition of soy lecithin to the inoculum support to accelerate the development of *Rhizobium japonicum*.

Several types of solid inocula supports have been assessed as possible alternatives to peat, including the encapsulation of microorganisms in polymer matrix microparticles, enabling the immobilisation of said microorganisms and facilitating their production, storage and handling (Cassidy M. B., Lee H. et Trevors J. T. 1996—J. Ind. Microbiol. 16:79-101). The French patent FR2590904 (Apr. 12, 1985) describes the incorporation of filamentous microorganisms in calcium alginate beads which are dispersed into the soil as a gel following the rehydration of the beads with a buffer, for example a phosphate buffer. The patent application WO 00/59949 (Jun. 4, 1999) describes an anti-fungal associated with a chitosan matrix. Chitin is also described as a bacterial bio-fertilisation support by the French patent application FR 2 941 589 A1 (Feb. 3, 2009). Although highly effective, chitin presents two problems: its prohibitive cost and its rather uncertain availability and restriction to a limited geographical area.

Also, supports made from plant material have already been alluded to (Smith R. S 1992—J. Microbiol. 25: 739-745). This idea is confirmed by the patent applications FR 2 593 11 (1996) and EP 0236 156 A2 (Jan. 17, 1986), which describe an inoculum support made from dried and ground grape pulp. Thistle is also used by certain authors.

To use these supports, they must undergo a series of operations. These are:
 drying in a 70° C. oven for 48 hours,
 grinding into pellets or powder,
 neutralisation to a pH adjusted to between 6.8 and 7 by the addition of $CaCO_3$.

However, all of these inoculum supports are, in particular, limited to the transport and storage of microbial cells and do not ensure their continued multiplication, even when development accelerator elements are incorporated with the microorganisms to facilitate the start of the development cycle once there are sufficiently favourable conditions in the soil. In fact, the water absorption capacity of these supports is relatively limited to a water-content-to-weight-ratio of: 17.5% for peat, 23.5% for France peat, 17.8% for kaolinite, 19.25% for vermiculite and 26.25% for thistle. According to Saint-Macary and Neyra (1992), the optimum necessary volume of liquid inoculums which can be absorbed into the support is generally between 60% and 70% of the water retention volume, which further limits the capacity of the quoted supports.

According to the works of Stephens and Rask (2000), it has to be noted that the support must have two fundamental properties: it must enable the growth of the microorganisms in place and maintain them over an acceptable conservation period. Microorganism multiplication is not sought in this case.

The European patent EP 0 443 040 B1 (Sep. 5, 1990) describes another type of microorganisms culture system, which uses a non-woven textile coated or impregnated with a nutrient solution in a culture medium containing microorganisms which are infectious to plant vermin. The impregnated textile is dried, and then rolled in several layers around the stem, the branch or the trunk of the tree to be treated. This exclusively external system remains subject to climatic variables, which will have a direct effect on the microbial culture. The cultivated microorganisms do not require any symbiotic activity with the plant treated.

Similarly, the U.S. Pat. No. 5,786,188 (Jul. 28, 1998) describes the preparation of a microscopic fungus inoculum. This inoculum is composed of a plant-based fibrous substrate, in pellets coated with a suspension of microscopic fungus in a hydrogel, an alginate or an alginic acid. The nutrients are loaded in the pellets, but nutriments serve only for the development of the microorganisms on the surface, which are exclusively fungus. This type of fungus-specific support cannot be used for bacterial culture, which develops in a closed or semi-closed environment.

As such and in regard to the state of the art, there is a need to provide a solid inoculums carrier, whose support provides at minimum the fundamental functions listed below. It must be, simultaneously, a:

storage and conservation support for viable microorganisms, transport support for microorganisms providing the best possible handling conditions, growth support for the regrowth of microorganisms, support for the multiplication of the regrown microorganisms, support for the protection of the microorganisms against the elements in the interstitial medium, support for the protection of microorganisms and their culture medium from the effects of soil leaching, support for the protection of microorganisms from hydric stress.

The said functions offer the advantage of obtaining a significant and long-lasting density of microorganisms in the interstitial medium, in order to optimise for example the symbiotic relationship between the root system and the microorganisms or the biotic impact which stimulates the plant's development and productivity, or to provide the plant with protection.

In order to better understand the invention, the term "superabsorbent variable-volume agro-pellet", in singular or in the plural, refers to a granulate obtained by chemical and thermomechanical treatment using an extrusion system fitted with two co-rotating endless screws which perform plasticization by mixing, shearing and pressurising plant-based polymers, and with a large capacity for absorbing water or aqueous solutions by increasing their volume without disintegrating, and returning to their initial volume once dehydrated.

The term "natural minifermenter" in singular or in plural, refers to a superabsorbent variable volume agro-pellet in which is stored a nutritive medium or anhydrous nutritive culture medium, used by viable microbial cells introduced into said agro-pellet in order to grow then multiply once the hydric conditions have been met due to the introduction of water. The microorganisms produced can migrate out via the porous structure of said agro-pellet.

The term "continuous natural minifermenter" in singular or in plural, refers to the previously described minifermenter in which a repeated dose of water solubilises the nutritive culture medium in a continuous manner, enabling its renewed availability for the microorganisms, which can then continue to multiply. It is understood that said microorganisms, throughout the course of their production, will migrate from said minifermenter into the interstitial medium and towards the root system in order to be brought into a symbiotic relationship with the plants.

The term "interstitial medium" refers to the space in the soil between the solid inoculum carrier and the plant's root system.

Figure 1:
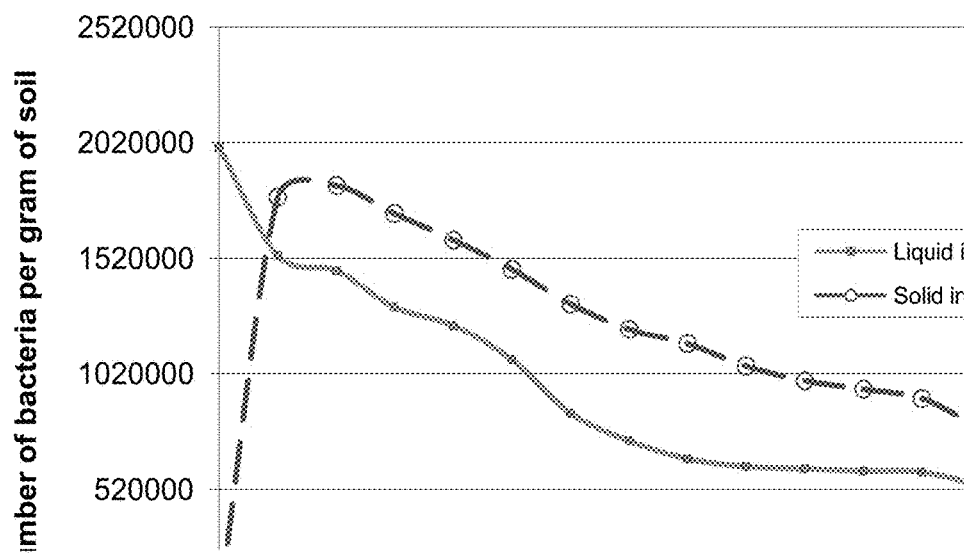
FIG. 1 represents the compared development curves of two inocula: liquid inoculum and $1/100^{th}$ solid inoculum carrier.

The patent application FR 2990943 (May 22, 2012), filed by the applicant of the present patent, describes a superabsorbent variable volume agro-pellet with the particularity of being able to absorb and store in reserve a large quantity of water or aqueous solution, reaching 500% of its weight, without disintegration and without percolation.

The present invention provides a way to overcome the disadvantages of the previously described inocula systems using a superabsorbent variable volume agro-pellet which functions as a natural minifermenter, able to absorb a substance or microscopic elements in a hydric suspension without losing them through soil leaching. In particular, the aim is to be able to manufacture a solid inoculum carrier system in said agro-pellet, performing simultaneously the roles of support and fermenter and enabling the multiplication within the agro-pellet of the microorganisms composing said inoculum, for which the various nutrients and growth factors of the nutritional medium are already present in a dry state within said minifermenter, without the risk of loss through soil leaching. The said solid inoculum carrier system is then packaged in such a way as to increase its effectiveness and biological activity.

According to the invention, the production of a new type of solid inoculums carrier proposed in large quantities, in a biodegradable support with its nutritional medium present in sufficient quantity and also in dry form, in which the microbial cells can regrow then grow and multiply as in a conventional fermenter, as soon as the support is rehydrated, including when said support is interred. The choice of fixed value microorganisms which are used to compose the inoculum must take into consideration the fact that these must be capable of multiplying in a closed environment, and are able to migrate out of the minifermenter using their inherent biological affinity with the plant's root system.

The aim of the invention is to create a solid inoculum carried in a superabsorbent, variable volume agro-pellet which works as a natural minifermenter, preloaded with an anhydrous nutritive medium to promote the growth then continued multiplication of the regrown microbial cells by the progressive rehydration and dissolution of said nutritive medium, avoiding soil leaching by rain and irrigation and stabilising this biological source in order to increase its effectiveness and biotic activity time.

A primary aspect of the invention therefore concerns a solid inoculum carried in a superabsorbent, variable volume agro-pellet which functions as a natural continuous minifermenter preloaded with a concentrated anhydrous nutritive medium to promote the continuous multiplication of a low-density supply of regrown microorganisms, for increased effectiveness and biological activity time. As such, said inoculum provides a number of fundamental properties enabling the:

a. conservation and storage of viable microorganisms, b. transport of microorganisms in the best possible conditions for handling and field application, c. growth of the regrown microorganisms for a continuation of the development cycle once there are sufficiently favourable conditions, d. intra-support multiplication of the microorganisms, e. protection of the microorganisms from negative elements in the interstitial medium, f. protection of the microorganisms and their culture medium from soil leaching effects, g. protection of the microorganisms from hydric stress.

According to the invention, said support is a superabsorbent, variable volume agro-pellet obtained according to the procedure described by patent application FR 2990943. It offers an improvement on the technological procedure because it does not require the operations described for the conditioning of the already known supports described in the state of the art. Essentially, it has to be noted that:
- its pH, for example, is already adjusted during production,
- it offers a regular particle size which facilitates handling and field application using commonly-used agricultural tools,
- the plastic structure gives it the ability to vary in volume by swelling with the absorption of water or aqueous solution and retracting with the loss or desorption of said liquids, enabling it to avoid disintegration under these conditions,
- the capacity to vary in volume with the absorption of water or an aqueous solution promotes rapid regrowth and microorganism multiplication in the porous structure, in contrast to what happens in rigid porous materials, in which microorganisms suffocate,
- its considerable capacity for water or aqueous solution absorption, in association with its high water or aqueous solution retention capacity, enable it to avoid the percolation of the liquid retained and therefore avoid the leaching of suspended or dissolved elements, while preserving the microorganisms from hydric stress thanks to the presence of water in said support which is always sufficient but never excessive,
- the extensive pores network promotes the migration of the microorganisms from the inside to the outside via pressure difference or via the effects of biotic agents.

The production process for said superabsorbent, variable volume agro-pellet according to FR 2990943 consists of elaborating a biodegradable plastic composite matrix composed of a mixture of plant-based protein biopolymers (e.g. cakes of sunflower, soy, colza, alfalfa or linseed), rich-starch saccharide biopolymers, hemicellulose and pectin, and natural rich-hyaline tissues or hydrocyst cells (e.g. sphagnum).

More precisely, the solid inoculum carrier prescribed by the invention presents a dry matter content ratio of between 92% and 95%, as well as a large capacity to absorb and reserve water or an aqueous solution, thanks to a power of absorption of up to 500% of its weight, enabling intense internal biological activity and giving it the role of a minifermenter. The said support stops absorbing once the absorption limit is reached, protecting it from percolation and therefore from leaching as the aqueous solution absorbed is retained within the structure.

The production of said natural minifermenter agro-pellet is, according to the invention, performed by preloading the superabsorbent, respiring agro-pellet with a concentrated nutritive liquid medium corresponding to the type of microorganism to inoculate, then dehydrating it before incorporating the said microorganisms in liquid form, the dehydrating it once more before packaging it for storage.

The agro-pellet made in compliance with the invention presents a matrix created by the plasticisation of natural materials using a twin-screw extrusion system and includes:

a). a mixture of biopolymers comprising:
  i. 55% to 60% by weight of protein biopolymers rich in globulins, albumins, prolamins and also rich in fibre, chosen from the by-products of high-protein plant matter (sunflower, soy, colza, alfalfa, linseed) and
  ii. 40% to 45% by weight of polysaccharide biopolymers rich in starch, hemicellulose and pectin, chosen from grain flours or sugar beet pulp, b). 5% to 40% by weight of a solid mixture of natural hyaline or hydrocyst cell tissue, chosen from living plant material: sphagnum or *Carduus* thistle.

According to a preferred composition which leads to the best results according to the invention, the nutritive medium is adapted to the strain of microorganisms to inoculate and formulated according to a composition, chosen optionally from:

a) YMB (Yeast-Mannitol-Broth) (Vincent, 1970),
b) YM (Yeast-Mannitol),
c) BHI (Brain Heart Infusion), but also any other adequate environment, considering the microorganisms to be processed.

According to the embodiment of the invention, the nutritive culture medium incorporated into the minifermenter support is in an aqueous phase, of which the dry matter ratio, composed of various nutrients and growth factors which are particularly favourable to the strain of microorganisms to inoculate, is 2 to 10 times higher than that of the liquid culture medium adapted according to the standards recommended for the same strain of microorganisms. Advantageously, the volume of the concentrated nutritive liquid medium to incorporate into said support may vary from 25% to 500% of its weight.

The concentrated nutritive medium is characterised by the fact that, at an equal final volume, it contains 2 to 10 times more nutrients and/or elements, which promote the growth and multiplication of the microorganisms in the culture than a normal nutritive medium. Said elements and/or nutrients are well known by the person skilled in the art, according to the types of microorganisms in the culture. Examples of these are yeast extract, simple sugars such as mannitol, glucose or sucrose, salts such as sodium chloride, magnesium sulphate, etc.

The microorganisms concerned by the invention may be, but are not limited to, mycorrhizal fungus, rhizobacteria and any other microorganisms which can contribute to the improvement of a plant's life, protection and biotic treatment such as: *Azotobacter* spp., *Acidovorax facilis, Flavobacterium* spp., *Pseudomonas* spp., *Rhodococcus rhodochrous, Bacillus subtilis, Bacillus chitinoporus, Bacillus laterosporus, Bacillus thuringiensis, Saccharopolyspora spinosa, Meterhizium anisopliae* or *Beauvaria bassiana.*

According to an embodiment of the invention, the water or aqueous solution absorbed in small quantities within the minifermenter will only partially dissolve the highly concentrated dry culture medium, following the physicochemical laws of dissolution, enabling the stored viable microbial cells to use these to grow and multiply. As such, according to an embodiment of the invention, the presence of the nutritive medium enables rapid microbial cell regrowth. The partial dissolution of the anhydrous nutritive medium ensures that there is a reserve available for the continuation of the microbial cell production cycle in the minifermenter. The presence of the dry nutritive medium in the minifermenter also contributes to the optimisation of the volume of water stored, providing beneficial hydric activity for the microorganisms. Excessive hydric activity can lead to increased microbial cell mortality.

The microbial cells produced inside the minifermenter, according to the invention, migrate via the porous structure of said minifermenter into the interstitial medium and the root system of the receiver plant throughout the duration of their production, thanks to the symbiotic relationship and the biological systems of the microbial cells and the receiver root system. As such, the production cycle of the microbial cells in said minifermenter can continue as long as there is a supply of water and a dissolved nutritive medium accessible to the microorganisms with an adapted water activity, as the metabolites produced by the microbial cells within the minifermenter are exported by the migration of living cells to the interstitial medium. However, the quantity of water or aqueous solution able to be absorbed into the support is naturally limited by the limited power of absorption and also by the presence of the anhydrous nutritive medium in said agro-pellet.

According to an embodiment of the invention, once the minifermenter is implemented and continuously functional, it enables users to considerably reduce the density of viable microbial cells to inoculate into said support to a density of between $1/500^{th}$ and $1/10^{th}$ of the quantity recommended by the standards for liquid inoculum, but preferentially to a density of between $1/200^{th}$ and $1/100^{th}$ of said quantity recommended by the standards for liquid inoculum. This density will rapidly increase to the density recommended by the standard in just a few days. For a liquid inoculum, the recommendation recommends a *Rhizobium* density of between $10^6$ and $10^8$ cells/ml (Padmanabhan Somasegaran et Jake Halliday, Applied and Environmental Microbiology, vol. 44, 1982). The standards indicate, for example, a number of *Rhizobium* spp. per gram of support of at least $5 \times 10^8$ cells (Beck et al., 1993). According to the invention, by inoculating for example $n \times 10^4$ cells per gram (n varying between 2 and 9) in the minifermenter, the recommended viable cell density is obtained in 3 to 5 days in the interstitial medium, representing a very important gain in inoculum support volume for a lower operational cost in comparison to the yields expected for the supply of development factors for the plant, or in the scale of the antagonistic action towards phytopathogenic agents. The maximum recommended density of viable cells for a solid inoculum carrier is $10^6$ cells per gram of support (Technical file for symbiotic nitrogen fixing—United Nations Food and Agriculture Organisation (FAO)—1992).

Unexpectedly, the level of production of microbial cells using the minifermenter in compliance with the invention, using $n \times 10^4$ cells per gram of support, reaches values of between $n \times 10^9$ cells and $n \times 10^{10}$ cells per gram of support over a variable length of time, depending on the sequences of water supply and the microbial strain inoculated, which is significantly higher than the standard recommended by the FAO manual's recommendation, which is $n \times 10^8$ cells per gram of support. It has to be noted that an increased effectiveness and biological activity period expressed by a bio-increase of the microbial population, which can then multiply intra-support from $n \times 10^4$ cells to $n \times 10^6$ additional cells to reach, within the space of 3 to 5 days, densities in the order of $10^{10}$ CFU (Colony Forming Units) in the soil sown with the inoculated support.

As such, the support in compliance with the invention functions as a genuine fermenter, in which microorganisms grow and multiply quickly, starting from a low density and rapidly reaching and even exceeding the microbial density values recommended by the standards according to the FAO manual's recommendations.

According to the invention, the capacity of the minifermenter to retain water enables the system to avoid the leaching of both the culture medium and the microbial cells through rainwater or irrigation. The solid inoculum carrier maintains itself near the root system and in this way increases the yields of the symbiotic relationships between the plant's root system and the microbial cells used to colonise it.

According to a second embodiment aspect of the invention, the solid inoculum, carried in a superabsorbent, variable volume agro-pellet which functions as a natural minifermenter in compliance with the invention, is obtained by the process which consists of:

a) incorporating the concentrated nutritive liquid medium adapted for the strain to inoculate into the superabsorbent, variable volume agro-pellet, at a rate of between 25% and 500% by weight, but preferentially at a fixed usage value rate adapted to the microorganisms;

b) dehydrating the support obtained in a) between 40° C. and 55° C. until the dry matter content reaches a level between 90% and 95% by weight;

c) sterilising the dry support obtained in b) in air-tight containers;

d) incorporating the previously cultured microbial strain into the sterile support obtained in c) with a microbial density varying between $1/500^{th}$ and $1/10^{th}$ of the quantity recommended by the standards for a liquid inoculation of the same strain, but preferentially a microbial density of between $1/200^{th}$ and $1/100^{th}$ of the quantity recommended by the standards for a liquid inoculation of the same strain;

e) dehydrating the support loaded in d) by a dry heat at a temperature between 35° C. and 40° C. to obtain a solid inoculum carrier at a dry matter content of between 90% and 95% by weight;

f) packaging the solid inoculum carrier obtained in e) to avoid contact with humidity.

According to an embodiment of the invention, the incorporation of the concentrated nutritive liquid medium as the biomass to be inoculated into the support is performed, preferentially, by sprinkling, but it can also be accomplished using spraying or rapid soaking.

According to an embodiment of the invention, the sterilisation of the agro-pellets is performed in an autoclave, by irradiation or by tyndallisation.

The solid inoculum carried in a superabsorbent, variable volume agro-pellet which functions as a minifermenter according to the invention presents a number of advantages. The first is convenience; it can be safely stored and transported in hermetically sealed packaging, in order to be easily applied according to the farmer's availability, using standard agricultural equipment. It is not wind-borne and does not saturate the soil because it is biodegradable. It lets the user avoid leaching of both the microbial population which is useful to the burgeoning root system and the culture medium required for the said microbial population. The incorporated nutritive medium plays both the role of starter to launch the cycle and also of culture medium for the continued intra-support multiplication of the strain of microorganisms inoculated. It protects the microbial biomass from hydric stress by keeping development inside the support.

The use of the solid inoculum carrier as a minifermenter according to the invention enables the producer to minimise the quantity of inoculum needed for application, providing significant savings in terms of microbial biomass production management using a specific strain. It also protects the microbial strain from the negative effects of the soil, such as its pH and chemical composition, which also has a significant influence on the pH.

The following examples will illustrate the invention and to facilitate comprehension of its various advantages. For convenience, in the following text, the following abbreviations will be used:

CFU: colony forming unit

YM: nutritive liquid medium (Yeast Mannitol)

YM2×: nutritive liquid medium 2 times stronger than the YM liquid medium

Example 1—Comparison of the Development in the Ground of a Liquid Inoculum and an Inoculum Loaded into a Minifermenter Support A superabsorbent, variable volume agro-pellet made from sunflower and sphagnum cake manufactured in the laboratories of the applicant was used, with an absorption capacity of 500% its weight in liquid.

The strain used is a soil bacterium of the genus *Rhizobium*: *Rhizobium phaseoli* DSM 30137 of the DSMZ collection (deutsche Sammlung von Mikroorganismen and Zelkulturen).

The nutritive culture medium used is specific to this strain, whose composition is described in tables 1 and 2. The concentration of nutritive liquid culture medium (YM) is that which is normally used for the culture of the strain being used, while the concentration of the nutritive culture medium (YM2×) destined to be incorporated into the support is twice the normal culture concentration (YM).

TABLE 1 composition of the YM nutritive liquid medium

| Product | Supplier | Reference | Concentration |
| --- | --- | --- | --- |
| Yeast extract | BIOCAR | A1202GC | 0.4 g/L |
| Mannitol | PROLABO | 25311.297 | 10.0 g/L |
| $K_2HPO_4$ | PROLABO | 26931.263 | 0.5 g/L |
| $MgSO_4, 7H_2O$ | SIGMA | M1880 | 0.2 g/L |
| NaCl | PANREAC | 121659, 1211 | 0.1 g/L | pH adjusted to 7.0 ($H_2SO_4$), autoclave sterilisation for 20 minutes at 121° C.

TABLE 2 composition of the YM2x nutritive liquid medium

| Product | Supplier | Reference | Concentration |
| --- | --- | --- | --- |
| Yeast extract | BIOCAR | A1202GC | 0.8 g/L |
| Mannitol | PROLABO | 25311.297 | 20.0 g/L |
| $K_2HPO_4$ | PROLABO | 26931.263 | 1.0 g/L |
| $MgSO_4, 7H_2O$ | SIGMA | M1880 | 0.4 g/L |
| NaCl | PANREAC | 121659, 1211 | 0.2 g/L | pH adjusted to 7.0 ($H_2SO_4$), autoclave sterilisation for 20 minutes at 121° C.

1 gram of agro-pellet is sprinkled with 1 milliliter of concentrated nutritive liquid medium YM2× for incorporation, providing an incorporation of 100% of the weight of the agro-pellet in YM2×. Then the agro-pellet is dried to 92% dry matter by weight.

Next, $10^6$ bacteria are inoculated ($1/100^{th}$ of the quantity recommended by the standards for a liquid environment), again by sprinkling onto the agro-pellets in order to obtain a solid inoculum carrier.

Batches of 100 g of ground and sterilised soil are prepared, which are then poured into square 1 dm² Petri dishes. The batches are then divided into two groups:

- Group 1 (referred to as TEST No 1) with batches of 100 g of soil inoculated with 1 g of solid inoculum carrier, around $10^6$ bacteria/dm² or $10^4$ bacteria/g of soil.
- Group 2 (referred to as TEST No 2) with batches of 100 g of soil inoculated with a liquid inoculum, for $10^6$ bacteria/dm² or $10^4$ bacteria/g of soil.

5 ml of sterile tap water is sprayed onto the surface of the soil and is left to incubate at 28° C. The soil is watered in an identical fashion every day.

After 5 days of testing, the bacteria in each batch are counted and the averages in TEST No 1 and TEST No 2 are compared.

In TEST No 1, the average content is around $3.4 \times 10^{10}$ CFU/dish. In comparison, in TEST No 2, the average content is around $1.5 \times 10^{10}$ CFU/dish, which is less than half of the average for TEST No 1. This shows a very significant difference of around $1.9 \times 10^{10}$ UFC/dish.

The superabsorbent respiring agro-pellet has therefore performed its role as a fermenter.

Figure 2:
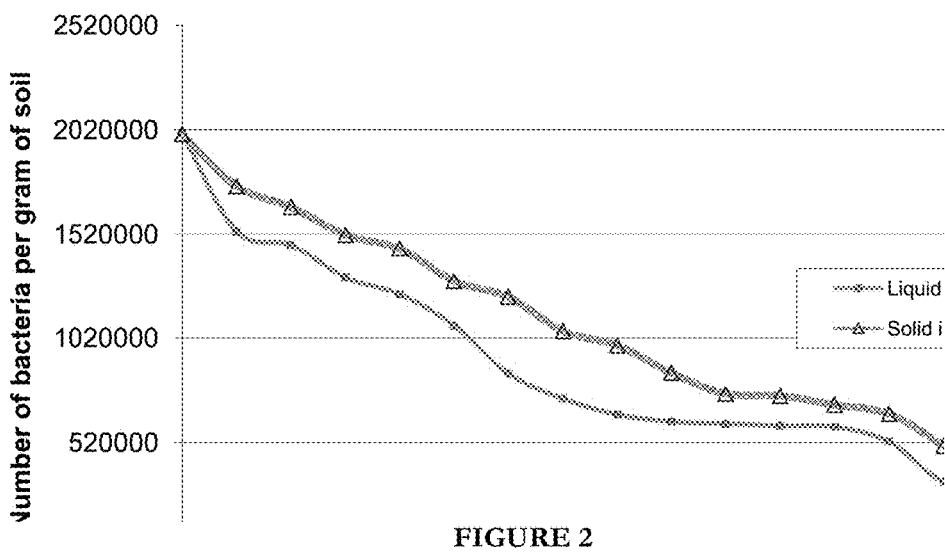
FIG. 2 represents the compared development curves of two inocula: liquid inoculum and 1/1 solid inoculum carried.

Example 2—A Comparative Study Between 3 Inocula Over a Long Period of time: Liquid Inocula, Solid Inoculum Carrier with $1/100^{TH}$ of the Liquid Inoculum and a Solid Inoculum Carrier at 1/1 of the Liquid Inoculum (FIGS. 1 and 2)

The sample soil used for the culture was taken from a regularly farmed field.

For the solid inoculum support, the superabsorbent respiring agro-pellets manufactured in the AB7 INNOVATION laboratories is used.

Soil bacteria of the genus *Rhizobium* and the strain *Rhizobium leguminosarum* CPI 106959 from the "Institut Pasteur" are used.

The nutritive liquid culture YM is used, whose composition is given in table 3, for the strain culture and as a constituent of the liquid inoculum. The YM2× nutritive culture medium is used to enrich the support before inoculating with bacteria; its composition, provided in table 4, indicates that it is twice as concentrated as the YM liquid medium.

TABLE 3

Composition of the YM nutritive liquid medium

| Product | Supplier | Reference | Concentration |
| --- | --- | --- | --- |
| Yeast extract | VWR | VM445253.224 | 1 g |
| Mannitol | VWR | K93281282.239 | 10 g |
| Soil extract | AB7 INNOVATION | ECH4158T | 200 ml |
| Distilled water | AB7 INNOVATION | ECH4158E | 800 ml | pH adjusted to 7 ± 0.2 ($H_2SO_4$), autoclave sterilisation for 30 min at 110° C.

TABLE 4

Composition of the YM2x nutritive liquid medium

| Product | Supplier | Reference | Concentration |
| --- | --- | --- | --- |
| Yeast extract | VWR | VM445253.224 | 2 g |
| Mannitol | VWR | K93281282.239 | 20 g |
| Soil extract | AB7 INNOVATION | ECH4158T | 200 ml |
| Distilled water | AB7 INNOVATION | ECH4158E | 800 ml | pH adjusted to 7 ± 0.2 ($H_2SO_4$), autoclave sterilisation for 30 min at 110° C.

a. Preparation of the Soil

The culture soil is placed in an air-tight container for sterilisation in a dry heat at 110° C. for four days. It is then distributed into 90 batches of 100 g.

b. Preparing the Tests 90 sterile pots of 125 ml were used, measuring 6.5 cm in diameter and 5.3 cm in height, with holes pierced in the base to enable excess irrigation water to drain out. They were split into three groups of 30 pots: group 1 for the liquid inoculum, group 2 for the agro-pellets inoculated at $1/100^{th}$ of the liquid inoculum and group 3 for the agro-pellets inoculated at 1/1 of the liquid inoculum. The result was a distribution of bacteria in the pots as described in table 5:

TABLE 5

Distribution of the bacteria in the pots of soil

| Test group | Inoculum | Number of bacteria per gram of soil |
|---|---|---|
| 1 | Liquid inoculum | $2 \cdot 10^6$ |
| 2 | Agro-pellets at 1/100$^{th}$ of the liquid inoculum | $2 \cdot 10^4$ |
| 3 | Agro-pellets at 1/1 of the liquid inoculum | $2 \cdot 10^6$ |

Then the experiment proceeded as follows:

In each pot was uniformly placed 80 g of sterile soil;

The inoculum was uniformly dispersed at a rate of 1 ml for liquid at $2 \cdot 10^8$ cells and 1 g of agro-pellet inoculated at $\frac{1}{100}^{th}$ (so $2 \cdot 10^6$ cells) and at 1/1 (so $2 \cdot 10^8$ cells) per 100 g pot of soil;

This was covered with the remaining 20 g of soil, then compacted it slightly;

It was watered with 15 cm$^3$ of distilled water and placed the samples in a dry heat at 28° C.

c. Monitoring the Tests

For each group, the pots were watered with 15 cm$^3$ of water every two days and 25 cm$^3$ of water on the last days of the week. Every four days, 2 pots from each group were sampled to count the number of bacterial cells. To do this:

All of the contents of the pot were mixed in a mixer to ensure complete homogenisation, then removed 5 g and placed in a test tube;

10 ml of sterile water was poured into the tube, then agitated vigorously using a vortex;

It was left to decant, then the supernatant was taken for CFU counting and observation and counting under a microscope. The CFUs were produced on agar in Petri dishes.

d. Analysis of the Results

The results obtained after 45 days of testing are illustrated by the graphs in FIGS. 1 and 2 which represent the development curves of the three inocula: liquid inoculum, solid inoculum carrier at $\frac{1}{100}^{th}$ and solid inoculum carrier at 1/1. Their analysis led to the following conclusions:

1. Comparison of the development of the liquid inoculum and the solid inoculum carrier at 1/1, illustrated by FIG. 2, shows that starting from the same density of bacteria/gram of soil ($2 \times 10^6$), the solid inoculum carrier showed better resistance. This demonstrates that the support plays a protective role for the microbial population, protecting them from negative elements in the soil such as the pH, but also environmental elements such as leaching by irrigation water, the excess of which passes through the holes pierced in the base of the pot.

2. The observation that the development of the solid inoculum carrier at $\frac{1}{100}^{th}$ demonstrates the rapid multiplication of the bacteria in the agro-pellet, which is shown to function as a genuine fermenter. The dry nutritive medium loaded in the support dissolves upon irrigation and plays a significant role as a starter, and later improves microbial multiplication. The solid inoculum carrier at $\frac{1}{100}^{th}$ ends up exceeding the level of the liquid inoculum by the 5$^{th}$ day, remaining greater right up until the last day of the study (FIG. 1). It can therefore be concluded that the minifermenter created in this way played both a role of protector of the microbial population, but also of a nutritive culture medium upon which the bacteria continued to rely in order to multiply.

3. The compared development of both solid inocula carrier, at 1/1 and $\frac{1}{100}^{th}$, shows up the phenomena inherent in closed-fermenter fermentation:

a. An excessive microbial cell density in a fermenter leads to cell mortality due to the metabolites produced by the biomass. This mortality is attenuated by the renewal of the culture medium. This is the case for the solid inoculum carrier whose culture medium is renewed with each watering.

b. Microbial multiplication is more conclusive when starting with a lower cell density for the same fermenter volume. With $\frac{1}{100}^{th}$ of the inoculum, better results are obtained while making considerable savings in the quantity of inoculum to use, providing a significant advantage in terms of cost.

In conclusion, the use of the natural minifermenter support provides microorganism protection from the negative elements in the soil and from leaching of the culture medium, without which there would be no continuity of the inoculum microbial cell production. Extraordinarily, the number of inoculated microbial cells at the start is reduced to $\frac{1}{100}^{th}$ of the standard level, representing a significant saving in both time and cost of the microbial strain culture.

The invention claimed is:

1. Solid inoculum carrier made of a superabsorbent biodegradable plasticized composite matrix agro-pellet capable of absorbing water or an aqueous solution up to 500% of its own weight, and having a porous structure, comprising:
    a) a mixture of biopolymer comprising
        i) from 55% to 60% by weight of a protein biopolymer comprising globulin, albumin, prolamin and fibre, chosen from a by-product of a plant matter comprising protein, selected from the group consisting of sunflower, soy, colza, alfalfa, and linseed plant matter;
        ii) from 40% to 45% by weight of a polysaccharide biopolymer comprising starch, hemicellulose and pectin, selected from the group consisting of grain flour and sugar beet pulp,
    b) from 5% to 40% by weight of a solid mixture of natural hyaline or hydrocyst cell tissue selected from the group consisting of sphagnum and *Carduus* thistle;
    c) an anhydrous nutritive medium; and
    d) an inoculum of microorganisms having a density of $10^4$ CFU/g to $2 \times 10^6$ CFU/g of the microorganisms;

wherein said agro-pellet is capable of increasing in volume up to a naturally limited volume to avoid percolation of said water or an aqueous solution and prevent leaching of said anhydrous nutritive medium, wherein said agro-pellet performs simultaneously the functions of support and fermenter, enabling the multiplication within the agro-pellet of the microorganisms of said inoculum.

2. Solid inoculum carrier according to claim 1, wherein said agro-pellet incorporates said anhydrous nutritive medium at a level between 25% and 500% of its own weight.

3. Solid inoculum carrier according to claim 1, wherein the anhydrous nutritive medium contained in the agro-pellet is enabled to be dissolved partially and progressively by rain or irrigation water with no risk of leaching.

4. Solid inoculum carrier according to claim 1, wherein said agro-pellet is enabled for partial and progressive dissolution of said nutritional medium upon rehydration, to promote sustained increase in continuous multiplication of the microorganisms therein, including when said agro-pellet is interred.

5. Solid inoculum carrier according to claim 1, wherein the agro-pellet has a dry matter content of between 92% and 95% its weight.

6. Solid inoculum carrier according to claim 1, wherein said agro-pellet is enabled to vary in volume without disintegrating by swelling via water or aqueous solution absorption and retracting by releasing these said liquids without disintegrating.

7. Solid inoculum carrier according to claim 1, wherein the microorganisms are a mycorrhizal fungus or a rhizobacteria.

8. Solid inoculum carrier according to claim 7, wherein the microorganisms are an *Azotobacter* spp., an Acidovorax *facilis*, a *Flavobacterium* spp., a *Pseudomonas* spp., a *Rhodococcus rhodochrous*, a *Bacillus subtilis*, a *Bacillus* chitinoporus, a *Bacillus laterosporus*, a *Bacillus thuringiensis*, a Saccharopolyspora *spinosa*, a *Meterhizium anisopliae* or a Beauvaria *bassiana*.

9. Solid inoculum carrier according to claim 1, wherein the superabsorbent agro-pellet has a dry matter content of between 92% and 95% its weight.

10. Solid inoculum carrier according to claim 4, wherein said superabsorbent agro-pellet is enabled to vary in volume without disintegrating by swelling via water or aqueous solution absorption and retracting by releasing these said liquids without disintegrating.

11. Solid inoculum carrier according to claim 1, wherein said superabsorbent agro-pellet is enabled to vary in volume without disintegrating by swelling via water or aqueous solution absorption and retracting by releasing these said liquids without disintegrating.

12. Method for production of a solid inoculum carrier according to claim 1 consisting of the following steps:
  a) incorporating the liquid nutritive medium adapted to a strain to inoculate into:
    a first support comprising:
      a) a mixture of biopolymer comprising
        i) from 55% to 60% by weight of a protein biopolymer comprising globulin, albumin, prolamin and fibre, chosen from a by-product of a plant matter comprising protein, selected from the group consisting of sunflower, soy, colza, alfalfa, and linseed plant matter;
        ii) from 40% to 45% by weight of a polysaccharide biopolymer comprising starch, hemicellulose and pectin, selected from the group consisting of grain flour and sugar beet pulp, and
      b) from 5% to 40% by weight of a solid mixture of natural hyaline or hydrocyst cell tissue selected from the group consisting of sphagnum and *Carduus* thistle,
    at a level between about 25% and about 500% of its weight to obtain a second support;
  b) dehydrating the second support obtained in a) between 40° C. and 55° C. until the dry matter content reaches a level between 90% and 95% by weight, to obtain a dry support;
  c) sterilising the dry support obtained in b) in an air-tight container to obtain a sterile support;
  d) incorporating a liquid inoculum of microorganism into the sterile support obtained in c) to obtain a microbial density varying between $10^4$ CFU/g to $2\times10^6$ CFU/g to obtain a loaded support;
  e) dehydrating the loaded support obtained in d) by dry heat at a temperature between 35° C. and 40° C. to obtain a solid inoculum carrier having a dry matter content between 90% and 95% by weight;
  f) packaging the solid inoculum carrier obtained in e) so as to avoid contact with humidity.

13. Method according to claim 12, wherein the incorporation of the liquid nutritive medium into said support is performed by sprinkling, spraying or rapid soaking.

14. Method according to claim 12, wherein the nutritive medium incorporated into the support comprises Yeast extract, mannitol, $MgSO_4$, $7H_2O$, and NaCl.

15. Method according to claim 12, wherein the liquid inoculum of microorganisms is incorporated into the support by sprinkling or spraying.

16. Method according to claim 13, wherein the support is sterilized in an autoclave, by irradiation, or by tyndallisation.

* * * * *